United States Patent [19]

Khan et al.

[11] Patent Number: 4,851,233
[45] Date of Patent: Jul. 25, 1989

[54] SUSTAINED RELEASE FORMULATIONS

[75] Inventors: Sadath U. Khan, Mine Hill, N.J.; Reginald Phillips, Coral Springs, Fla.

[73] Assignee: Warner-Lambert Company, Morris Plains, N.J.

[21] Appl. No.: 915,482

[22] Filed: Oct. 6, 1986

[51] Int. Cl.⁴ .................. A61K 9/22; A61K 9/26; A61K 9/36

[52] U.S. Cl. .................. 424/480; 424/468; 424/469; 424/470

[58] Field of Search ............. 424/468, 469, 470, 480

[56] References Cited

U.S. PATENT DOCUMENTS

| | | | |
|---|---|---|---|
| 4,252,786 | 2/1981 | Weiss et al. | 424/495 |
| 4,309,404 | 1/1982 | De Neale et al. | 424/489 |
| 4,369,172 | 1/1983 | Schor et al. | 424/480 |
| 4,389,393 | 6/1983 | Schor et al. | 424/480 |
| 4,461,759 | 7/1984 | Dunn | 424/469 |
| 4,505,890 | 3/1985 | Jain et al. | 424/480 |
| 4,525,345 | 6/1985 | Dunn et al. | 424/470 |
| 4,555,399 | 11/1985 | Hsiao | 424/493 |
| 4,610,870 | 9/1986 | Jain et al. | 424/473 |
| 4,792,452 | 12/1988 | Howard et al. | 424/468 |

*Primary Examiner*—Shep K. Rose
*Attorney, Agent, or Firm*—Ronald A. Daignault

[57] ABSTRACT

A new drug delivery system, which gives sustained release properties is made by combining certain cellulosic polymers with cellulose in a binder system.

3 Claims, No Drawings

SUSTAINED RELEASE FORMULATIONS

BACKGROUND

The production of sustained release oral pharmaceutical formulations which exhibit controlled, but effective, solubility is a difficult task.

Freely soluble drugs, e.g., procainamide hydrochloride and sparingly soluble drugs, e.g., sodium meclofenamate and meclofenamic acid, are generally difficult to put into sustained release formulations.

THE INVENTION

It has been discovered that pharmaceutically active oral dosage forms having controllable release profiles, e.g., 8- and 12-hour profiles, can be produced using certain polymer/filler combinations in their formulations.

In one preferred embodiment, procainamide hydrochloride was mixed with a binder system which contains a hydroxyethyl cellulose, Type H, polymer, microcrystalline cellulose, sugar, silicon dioxide and magnesium stearate in water.

In another preferred embodiment, sodium meclofenamate was mixed with a composition containing hydroxyethyl cellulose, Type H, microcrystalline cellulose, calcium stearate, hydroxyethyl cellulose Type L, and water.

ADVANTAGES

The compositions and methods of the invention have several advantages over other sustained release formulations.

Principally, the instant formulations give 8- and 12-hour release profiles which are highly acceptable regardless of whether the drug(s) or other beneficial substance(s) contained in the product is sparingly or freely soluble in water or gastric juices.

Use of the instant compositions yield tablets which are:

(1) small (e.g., on the order of about 0.150–0.280 inch or less, (2) easily granulated, i.e., requiring no heating, as does the wax melt process, (3) capable of leaving no tablet residue after dissolution.

Overall, the instant formulations and processes which use them have higher economy and efficiency than other well-known tablets and processes, e.g., the wax matrix tablet.

Other aspects and advantages of the invention will become apparent after a consideration of the following description of the invention.

DESCRIPTION OF THE INVENTION

The formulations of the invention have three predominant components:
(a) a beneficial substance or drug,
(b) a polymeric binder, and
(c) a filler.

BENEFICIAL SUBSTANCES

The drug or beneficial substance to be administered via the oral dosage forms of the invention can be any of a wide variety of substances or materials which function to alleviate disease and/or symptoms related thereto as well as those which function to aid in the body's normal functions, e.g., digestion, growth and the like. Pharmaceutically active materials are preferred.

Thus, while the discussion herein centers on drugs, it should be understood that vitamins, minerals, hormones, and the like can also be administered using the subject formulations. Mixtures are operable.

In general, any health-promoting substance whose water solubility is such that it is compatible with the polymeric component of the formulation while maintaining the sustained-release properties to be attained may be used.

Preferred drugs to be employed include sparingly soluble drugs such as, sodium meclofenamate, meclofenamic acid, methyldopa, dilantin, and the like, and freely soluble drugs, such as diphenhydramine, HCl, pseudoephedrine HCl, and procainamide hydrochloride. Sodium meclofenamate and procainamide hydrochloride are highly preferred.

POLYMERS

The polymeric component of the instant formulations will generally contain water-miscible polymers. Those of cellulosic character, eg., hydroxy alkyl celluloses of moderate to high molecular weight are one preferred group of principal binders. Generally, molecular weights of about 650,000 to about 1,150,000 are preferred. Natrosol 250H, a Type "H" hydroxy ethyl cellulose polymer produced by Hercules, Inc. is highly preferred. Suitable hydroxy propyl cellulose polymers, such as those of Hercules Co., can be used. Other useful binders include Natrosol 250HH, Methocel E4M, Methocel K, Klucel, and the like.

Another preferred group of binders are the water miscible vinyl or addition polymers. One highly preferred type is polyvinylpyrrolidine, eg., Povidone of GAF.

Mixtures are operable.

The binding capacity of the principal binder can be enhanced via the use of a secondary binder. Useful secondary binders are generally low to moderate molecular weight cellulosic polymers. Generally, molecular weights of about 70,000 to about 85,000 are preferred. Like the principal binders, they too are hydroxyalkyl celluloses. Natrasol Type "L" a hydroxyethyl cellulose of Hercules Co. is a highly preferred secondary binder.

FILLERS

The filler(s) employed in the compositions of the invention are generally those which enhance binding capacity and assist in the controlled dissolution of the final dosage form in an aqueous environment.

Generally, useful fillers are sugar, lactose, silicon dioxide, and microcrystalline cellulose. It is generally preferred that from about 3 to about 10 percent by weight of the final formulation consist of microcrystalline cellulose.

OTHER EXCIPIENTS

The fillers discussed above are not true excipients in that they assist the binding and solution function of other ingredients. There will also be present, in the instant compositions, various quantities of conventional excipients such as sweeteners, e.g., sugar, colorants, processing acids, e.g., magnesium stearate, and the like one or more lubricant(s) can be used in the subject compositions.

The following table gives the relative quantities of the principal components of the inventive formulations. All percentages are approximations based on total composition weight, unless specified otherwise.

TABLE I

| Component | Percentage Range (Broad) | Percentage Range (Preferred) |
|---|---|---|
| Drug | 60–90 | 70–85 |
| Polymeric binder | | |
| Primary binder | 5–20 | 7–15 |
| Secondary binder | 0–3 | 0–0.5 |
| Filler | 5–15 | 7–15 |
| Excipients | 0–10 | 0–3 |
| Water | q.s. | q.s |

METHOD OF PREPARATION

A typical process for preparing tablets in accordance with the invention involves the procedures outlined in Method A and/or B for the cores. One typical procedure for coating is described below.:

METHOD A

Pass the drug through a screener, e.g. a Fitzmill, #N00 RH screen with impact at high speed. Load into a suitable planetary mixer, and hydroxyethyl cellulose and blend for several minutes, e.g. about 5 minutes until the blend has a loose density of about 0.38 g/ml.

Dissolve povidone in water and granulate the powder blend from above with this solution using additional water if needed to yield a wet granulate. Do not overwet.

Spread the wet granulate on paper-lined trays and dry in forced air ovens at 50° to 55° C. overnight to a L.O.D. of about 0.6% (±0.3%).

Add silicon dioxide and magnesium stearate and pass through a Fitzmill #2A RH screen with knives at medium speed (Mesh pattern, sonic sifter: sift 5, pulse 6). Load this mixture into a P-K blender and tumble blend for several minutes, e.g. about 5 minutes.

METHOD B (Alternate method using Collette Gral)

Pass drug through a Fitzmill #N00 RH screen with impact at high speed, then dissolve it in water.

Load the milled drug and the hydroxyethyl cellulose into a 75L Collette Gral. Blend with the mixer at 200 rpm and granulator at speed II for 3 minutes.

Granulate for 2 minutes. Add a sufficient quantity of purified water to make a satisfactory granulation.

Spread the last granulate onto paper-lined trays and dry in a forced air oven at 50°–55° C. over night to a L.O.D. of about 0.6% (±0.3%).

Add silicon dioxide and colarant to the dried product and pass through a Fitzmill, #2A RH screen with knives at medium speed. Load the milled product into a suitable P-K blender and tumble blend for 5 minutes.

Compress 855 mg of the product of Method A or B using 0.343"×0.750" elliptical punches at a hardness of about 15–17 kp and thickness of about 0.290". Use precompression.

COMPRESSION OF CORES

Method A:
| Screen No.: | 20 | 30 | 40 | 60 | 80 | 100 | Pan |
|---|---|---|---|---|---|---|---|
| % Retained: | 8.0 | 10.0 | 11.0 | 17.0 | 13.0 | 6.0 | 35.0 |

Method B:
| Screen No.: | 20 | 30 | 40 | 60 | 80 | 100 | Pan |
|---|---|---|---|---|---|---|---|
| % Retained | 9.0 | 20.0 | 24.0 | 28.0 | 6.0 | 4.0 | 9.0 |

Loose density of final granulation = 0.59 g/ml.

Method of Preparing Table Film Coating

Prepartion of Coating Solutions:

Color Coat: (Prepare about 150 g of solution to coat 1 kg of tablets).

Add antifoam AF Emulsion, medicinal to purified water and mix to create a vortex. Add colorant slowly into the vortex and mix for 30 minutes before using.

Clear Coat: (Prepare about 65 g of solution to coat 1 kg of tablets).

Dissolve vanillin and polyethylene glycol in purified water. Add hydroxy ethyl cellulose and mix until dissolved.

Application of Film Coat:

Apply about 2.5% w/w color coat and then 0.5% w/w clear coat by using the following guidelines in a 24" Accela Cota pan:

| | COLOR COAT | CLEAR COAT |
|---|---|---|
| Pan Load (kg) | 6 to 8 | 6 to 8 |
| Pan Speed (RPM) | 14 | 14 |
| Inlet Air Temp. (°C.) | 60–80 | 60–80 |
| Tablet Bed Temp. (°C.) | 37–39 | 37–39 |
| Fluid Nozzle | L3B | L3B |
| Air Nozzle | 66 PD | 66 PD |
| Atomizing Pressure (psi) | 40 | 40 |
| Cylinder Pressure (psi) | 50 | 50 |
| Spray Rate (ml/min) | 20–30 | 20–30 |

DRAWINGS

The drawings are graphs depicting in vitro dissolution studies of the tablets made in Examples 1 and 2. FIG. 1 shows the profile for 200 mg sustained release sodium meclofenamate tablets. FIG. 2 shows the profile for 750 mg procainamide hydrochloride sustained release tablets.

EXAMPLES

The following examples describe the production and dissolution of tablets produced using the compositions and processes of the invention.

Example 1

200 mg. sodium meclofenamate tablets were made using two formulations, an 8-hour release composition and a 12-hour release composition. Those compositions contained the ingredients and quantities listed in Table II.

TABLE II

Sodium Meclofenamate Formulations

| | Weight Percentage | |
|---|---|---|
| Ingredient | 8 hour release profile | 12 hour release profile |
| Sodium Meclofenamate | 82.30% | 74.30% |
| Microcrystalline Cellulose | 8.80% | 14.30% |
| Hydroxyethyl Cellulose NF Type "L" | 0.50% | 0.50% |
| Hydroxyethyl Cellulose NF Type "H" | 7.10% | 9.70% |

TABLE II-continued

Sodium Meclofenamate Formulations

| Ingredient | Weight Percentage 8 hour release profile | Weight Percentage 12 hour release profile |
| --- | --- | --- |
| Purified Water USP | q.s. | q.s. |
| Calcium Stearate NF | 1.30% | 11.20% |

The procedure used to produce the tablets was substantially that outlined above as Method B, along with the coating procedures described above.

The procedure used to conduct the dissolution studies was USP Method II with Paddler at 75 rpm in pH 8 phosphate buffer maintained at 37° C. temperature.

Example 2

Using procedures similar to those employed in Example 1, 750 mg. procainamide hydrochloride tablets were made and tested for dissolution.

The compositions used to make the tablets are given in Table III.

TABLE III

Procainamide Hydrochloride Formulations

| Ingredient | Weight Percentage 8 hour release profile | Weight Percentage 12 hour release profile |
| --- | --- | --- |
| Procainamide Hydrochloride | 83.30% | 83.30% |
| Hydroxyethyl Cellulose NF Type "H" | 11.10% | 14.40% |
| Microcrystalline Cellulose NF | 3.30% | — |
| Sugar USP, Granular | 1.60% | 1.60% |
| Silicon-dioxide | 0.20% | 0.20% |
| Magnesium Stearate NF | 0.50% | 0.50% |
| Purified Water USP | q.s. | q.s. |

As FIGS. 1 and 2 illustrate, the kinetics of drug release are approximately zero order for these formulations.

Based on this dissolution data, applicants theorize that the hydroxyethyl cellulose [HEL] polymer of higher molecular weight, type "H", is rapidly hydrated to a transient gel state, which persists long enough to provide a sustained dissolution. Drug release occurs via a slow diffusion and matrix erosion. Therefore, at the end of drug dissolution the tablet is completely disintegrated. Whereas, the HEL of low molecular weight, Type "L", is quickly hydrated to a monodispersed state, causing it to function as a disintegrant in tablet. HEL, type "L" is used as a binder in Meclomen SR. Applicants do not necessarily intend to be bound by this theory.

While the examples are directed to tablets, it should be recognized that other solid dosage forms are contemplated. Thus, pellets, granules, pastes and the like, can also be made using the technology taught herein.

Capsules containing pellets produced in accordance with the invention can be produced using conventional pellet and capsule technology.

Reasonable variations, such as those which would occur to a skilled artisan, can be made herein without departing from the scope of the invention.

We claim:

1. A compressed tablet binder system mixture consisting essentially of:
   (a) about 60-90 wt % of procainamide hydrochloride or sodium meclofenamate,
   (b) about 5-20 wt % of a Type "H" hydroxy ethyl cellulose, and
   (c) about 5-15 wt % of microcrystalline cellulose, which is further coated by the hydroxy ethyl cellulose; said hydroxy ethyl cellulose rapidly hydrating to a transient gel state which persists long enough to provide a sustained dissolution with drug release occurring via a slow diffusion and matrix erosion; said tablet being completely disintegrated at the end of drug dissolution.

2. The composition of claim 1 wherein (a) comprises procainamide hydrochloride.

3. The composition of claim 1 wherein (a) comprises sodium meclofenamate.

* * * * *